(12) United States Patent
McCormick

(10) Patent No.: US 7,888,132 B2
(45) Date of Patent: Feb. 15, 2011

(54) METHOD FOR PROCESSING TISSUE SAMPLES IN PREPARATION FOR HISTOLOGICAL EXAMINATION

(75) Inventor: James B. McCormick, Lincolnwood, IL (US)

(73) Assignee: Leica Biosystems Richmond, Inc., Richmond, IL (US)

( * ) Notice: Subject to any disclaimer, the term of this patent is extended or adjusted under 35 U.S.C. 154(b) by 367 days.

(21) Appl. No.: 11/742,647

(22) Filed: May 1, 2007

(65) Prior Publication Data
US 2007/0196891 A1 Aug. 23, 2007

Related U.S. Application Data

(62) Division of application No. 10/723,692, filed on Nov. 26, 2003.

(51) Int. Cl.
*G01N 1/30* (2006.01)
*G01N 1/00* (2006.01)
*C12M 1/34* (2006.01)
*B01L 3/00* (2006.01)

(52) U.S. Cl. .................. 436/174; 422/61; 422/102; 435/40.5; 435/287.1

(58) Field of Classification Search .............. 422/102, 422/61; 436/174; 435/287.1, 40.5
See application file for complete search history.

(56) References Cited

U.S. PATENT DOCUMENTS

| 3,537,636 | A | | 11/1970 | Rochette |
| 3,996,006 | A | | 12/1976 | Pagano |
| 4,225,557 | A | | 9/1980 | Hartl et al. |
| 4,367,750 | A | | 1/1983 | Levine |
| 4,420,353 | A | * | 12/1983 | Levine ............... 156/227 |
| 4,549,670 | A | | 10/1985 | Trendler |
| 4,557,903 | A | | 12/1985 | McCormick |
| 4,569,647 | A | | 2/1986 | McCormick |
| 4,576,796 | A | | 3/1986 | McCormick |
| 4,645,743 | A | * | 2/1987 | Baker et al. ............ 436/66 |
| 4,874,090 | A | | 10/1989 | Dyke |
| 5,080,869 | A | | 1/1992 | McCormick |
| 5,269,671 | A | | 12/1993 | McCormick |
| 5,338,358 | A | | 8/1994 | Mizusawa et al. |

(Continued)

FOREIGN PATENT DOCUMENTS

EP 0245969 11/1987

(Continued)

OTHER PUBLICATIONS

Office Action for U.S. Appl. No. 10/723,692 dated Mar. 1, 2010.

(Continued)

*Primary Examiner*—Lore Jarrett
(74) *Attorney, Agent, or Firm*—Thompson Coburn LLP

(57) ABSTRACT

A histological specimen retaining device for processing tissue. The histological specimen retaining device comprises a foldable permeable sheet having edges and a permeable target disposed on the foldable permeable sheet within the edges of said sheet thereby providing extended flap portions. The extended flap portions are foldable to overlap the target. The histological specimen retaining device also comprises a malleable securing strip attached to the permeable sheet of a length sufficient to secure said folded flap portions overlapping said target.

3 Claims, 2 Drawing Sheets

U.S. PATENT DOCUMENTS

| | | | |
|---|---|---|---|
| 5,662,639 | A | 9/1997 | Tanaka et al. |
| 5,665,398 | A | 9/1997 | McCormick |
| 5,812,312 | A | 9/1998 | Lorincz |
| 5,817,032 | A * | 10/1998 | Williamson et al. ......... 600/562 |
| 5,928,934 | A | 7/1999 | McCormick |
| 5,932,430 | A | 8/1999 | Larka et al. |
| 6,017,476 | A | 1/2000 | Renshaw |
| 6,060,039 | A | 5/2000 | Roe et al. |
| 6,372,514 | B1 | 4/2002 | Lee |
| 2005/0112032 | A1 | 5/2005 | McCormick |
| 2005/0112034 | A1 | 5/2005 | McCormick |
| 2009/0246825 | A1 | 10/2009 | McCormick |

FOREIGN PATENT DOCUMENTS

| | | |
|---|---|---|
| EP | 0807807 | 11/1997 |
| EP | 1321757 | 6/2003 |
| WO | PCT/US/2005042933 | 11/2005 |

OTHER PUBLICATIONS

Office Action for U.S. Appl. No. 10/723,692 dated Sep. 3, 2009.
Office Action for U.S. Appl. No. 12/425,583 dated Dec. 9, 2009.

* cited by examiner

METHOD FOR PROCESSING TISSUE SAMPLES IN PREPARATION FOR HISTOLOGICAL EXAMINATION

RELATED APPLICATION DATA

This application is a division of U.S. patent application Ser. No. 10/723,692, filed on Nov. 26, 2003.

FIELD OF THE INVENTION

The present invention is generally directed to a device and a method for processing tissue samples for histological examination. More specifically, the invention relates to an improved device and method for retaining and processing tissue samples with various fluids prior to embedding the tissue samples in paraffin or the like in preparation for microscopic examination.

BACKGROUND OF THE INVENTION

Standard procedures for preparing tissue samples for microscopic examination involve contacting the tissue sample with various fluids, embedding the tissue samples in paraffin, and slicing paraffin-embedded tissue samples very thinly with a microtome. Detailed examples of the preparation of tissue samples for histological examination are fully described in U.S. Pat. Nos. 5,080,869; 5,665,398; and 5,928,934; which are incorporated herein by reference.

In the practice of histopathology and the preparation of cellular tissue materials for examination with the microscope, preparatory steps have an important impact on the availability of microscopic details that form the basis of proof for a diagnosis. For example, it may be critical to maintain orientation of the tissue specimen during the preparatory phases. In addition, movement of the specimen during preparation, either during collection and transfer to the lab or during laboratory processing in a tissue processing cassette, may damage the specimen. Lastly, cross contamination may occur during the processing steps if a standard tissue sample processing cassette is utilized because very small specimens may slip through the usual openings of the cassette.

When tissue materials are collected, as with a biopsy, there are specific criteria or judgments made of what might be suspicious of showing a disease process. The "suspect" area of the biopsy is sampled with the intention of revealing a tissue diagnosis as the basis of a treatment method or approach. The contemporary methods of tissue biopsy, in the most modern approach, use image guidance techniques or with direct vision for surface lesions where a "punch biopsy" of skin or tumor surfaces are harvested, or needle "through cut" biopsies, or aspiration biopsies of fluid, or incision biopsies of surface lesions, or "remote" skinny needle biopsies with ultrasound, MRI, direct video or radio-graphic guidance to an imaging system that will provide imaging of "hidden" suspect tumor targets deep with body cavities or organs. The resultant "captured" tissue may be solid, semi-solid, or liquid, as with cavity fluids containing traces of surface cells, to be determined benign, malignant, or inflammatory.

It is of vital importance to orient the tissue in a fixed and precise way that will demonstrate anatomical relationship of importance to adjacent organ tissues or surfaces; all in relationship to the disease process. For instances, if a gastroenterologist or any other special-ologist visualized a suspicious area to biopsy, the ologist alone knows what was up or down, right or left, adjacent the stomach or other anatomical landmark.

Consequently, it is desired to produce a device to retain, orient, and prevent cross contamination of a tissue sample during the preparatory phases of a histological examination.

BRIEF DESCRIPTION OF THE DRAWINGS

FIG. 2a is shown with an exemplary tissue specimen.

SUMMARY OF THE INVENTION

The invention is directed to a histological specimen retaining device for processing tissue. The histological specimen retaining device comprises a foldable permeable sheet having edges and a permeable target disposed on the foldable permeable sheet within the edges of said sheet thereby providing extended flap portions. The extended flap portions are foldable to overlap the target. The histological specimen retaining device also comprises a malleable securing strip attached to the permeable sheet of a length sufficient to secure said folded flap portions overlapping said target.

The histological specimen retaining device may also have the malleable securing strip attached at an edge of the permeable sheet. The malleable securing strip may be a metal wire or a metal foil.

The target of the histological specimen retaining device may be coated with a release agent. The release agent may be a parting layer of gluten, gelatin, casein, alginate, or similar organic coating. Additionally, the target may be a permeable paper sheet.

The histological specimen retaining device may also comprise X and Y coordinate marking lines on the permeable target. The X and Y coordinate marking lines may allow for proper orientation of a tissue sample when placed on the target and serve as a scalable reference for optional photographic imaging.

The invention is also directed to a method of processing tissue specimens using the histological specimen retaining device. The method consists of placing a tissue sample on a histological specimen retaining device as described above. Then the sample is prepared as follows: folding the flap portions to overlap the target containing the tissue sample; crimping the malleable securing strip to clamp the folded flap portions to the permeable target; and processing the tissue preparation system for histological examination in known ways.

Additionally, the method of using the histological specimen retaining device may include adding a binder to the tissue sample on the target prior to the folding of the flap portions. The binder may be either agar or agarose.

These and other objects and advantages of the invention will become apparent through the following detailed description.

DETAILED DESCRIPTION OF THE PREFERRED EMBODIMENTS

Figure 1:
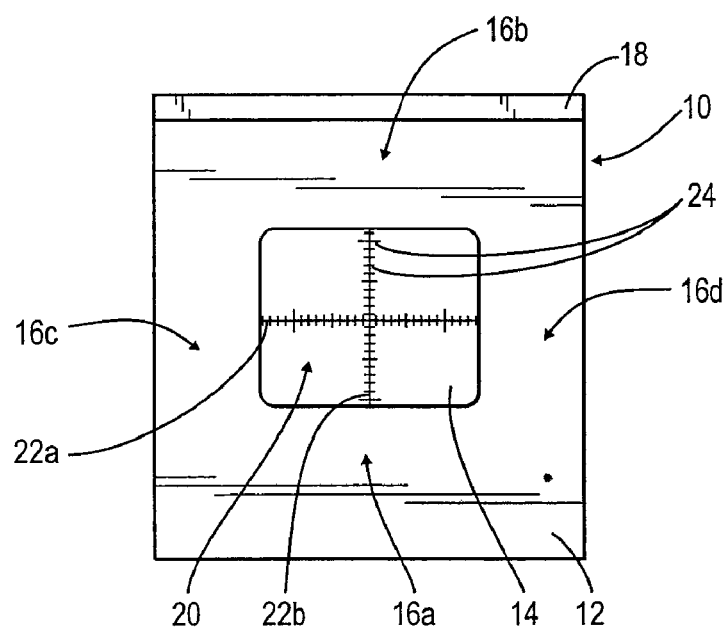
FIG. 1 is a top view of an exemplary histological retaining device embodying the features of the present invention.

Referring to FIG. 1, there is illustrated an exemplary histological retaining device 10 embodying the features of this present invention. Device 10 generally consists of four parts:

a permeable sheet 12, a permeable target 14, extended flap portions 16a-d, and a malleable securing strip 18.

More specifically on FIG. 1, permeable sheet 12 is a sheet of filter-type paper or similar porous paper that is permeable to processing fluids and/or molten embedding wax, but retains a tissue specimen during processing. Because permeable, filter-type papers come in a wide range of permeability, thickness, and strengths, many types of papers will work as permeable sheet 12 as long as the sheet is porous to the typical processing fluids used in histological preparation in an efficient manner according to routine histological procedures while retaining tissue specimens 1 mm or smaller in size.

Common lens paper is an example of a typical media suitable for permeable sheet 12; preferably, S/P lens paper provided by Allegiance (P1055) is an example of filter paper suitable as permeable sheet 12. Additionally, sheet 12 has a length and a width appropriate for the size of tissue specimen that is to be processed and also appropriate for the size of target 14 that is to be used such that the extended flap portions 16a-d are foldable to overlap target 14. Moreover, the size of sheet 12 may vary in relation to the size of the specimen to be processed. For example, it is preferred that permeable sheet 12 may be about 0.050 mm thick and about 55×58 mm if used with a permeable target 14 that is 22×28 mm.

Permeable sheet 12 generally consists of four integrally extended flap portions 16a-d. Each flap portion 16 extends beyond target 14, which is disposed on sheet 12, and each flap portion 16 is proportioned to be folded over or under target 14 one flap portion at a time. Each flap portion 16a-d has a length and width sufficient to overlap at least a portion of target 14 when folded. However, it is preferred that the length and width of flap portions 16a-d be sufficient to completely cover target 14 when folded. It is understood that because flap portions 16a-d must be folded to overlap target 14, permeable sheet 12 must be of a thickness that allows for the easy folding of each flap portion 16a-b as with "tea bag" like paper.

Again referring to FIG. 1, permeable target 14 is disposed on permeable sheet 12 within the edges of sheet 12. Target 14 is designed to support the tissue specimen during the preparatory phase of a histological examination. Target 14 has several key characteristics. First; permeable target 14 should have nominal dimensions to fit the existing popular TURBO-FLOW molds or tissue processing cassettes as described in U.S. Pat. No. 5,665,398, incorporated herein by reference. For example, permeable target 14 may be 24×37 mm, 24×30 mm, 15×15 mm, or 10×10 mm in size.

Second, permeable target 14 may be chipboard cardstock or perforated 302 stainless steel. If target 14 is a perforated stainless steel, it is preferred that target 14 has a 50-70% perforation of the surface with square 0.5-0.8 mm holes arranged to permit passage of processing fluids and molten wax in the fixation, processing, clearing, and infiltration steps of the tissue processing as commonly practiced in histology laboratories. However, other arrangements of holes and porosities that may allow for the passage of fluids and retention of samples will also work for target 14 when constructed out of perforated stainless steel.

Additionally, permeable target 14 may be a separate sheet of 0.5 mm thick chipboard card stock or other cellulose paper. The chipboard card stock preferably has a permeability similar to the tissue sample mounted on its surface. Additionally, the chipboard card stock is preferably coated with a release agent to assist in forming the separation of the card from its wax impregnated specimen-to be investment cast into the wax block. The release agent may be a parting layer of gluten, gelatin, casein, alginate, or similar organic coating.

Third, permeable target 14 is generally disposed within the edges of permeable sheet 12 and is preferably disposed near the center of permeable sheet 12. Target 14 may be loosely placed on or tacked to sheet 12. If target 14 is tacked to sheet 12, it may be fixed by a glue spot, but target 14 must be mechanically separable from sheet 12 through light pulling pressure with forceps that grasp target 14 after processing. Generally, any adhesive may be used for the glue spot as long as the adhesive is not soluble in the processing fluids typically used in histological sample preparation. For example, a hot melt polyolefin adhesive may be used for the glue spot.

Fourth, permeable target 14 may also contain a printed X/Y coordinate marking system 20 centered on target 14 as shown in FIG. 1. Marking system 20 consists of horizontal and vertical marking lines 22a and 22b along with measurement marking lines 24 spaced at equal distances on horizontal and vertical marking lines 22a and 22b. Any spacing of measurement marking lines 24 is appropriate, but 1 mm spacing is preferred. X/Y coordinate marking system 20 is designed to allow for proper orientation of a tissue sample when placed on target 14 and serve as a scalable reference for optional photographic imaging of the tissue specimen.

Again referring to FIG. 1, histological retaining device comprises a malleable securing strip 18. When extended flap portions 16a-d are folded to overlap target 14 (described in more detail below), malleable securing strip 18 is designed to hold, crimp, or clamp the folded extended flap portions 16a-d to target 14; thereby, securing the extended flap portions 16a-d in the folded condition. Additionally, malleable securing strip 18 provides positive release upon the opening of folded flap portions 16a-d after processing of the sample.

Strip 18 is attached to permeable sheet 12 by adhering means such as a double faced adhesive tape or a hot melt weld consisting of a vinyl wax co-polymer. Further, strip 18 may be fixed to sheet 12 by any suitable poly olefin adhesive or any other adhesive that is not soluble in the typical solutions used in histological sample preparation. While it is preferred that strip 18 be attached at the edge of sheet 12, other locations on sheet 12 are possible, as long as strip 18 can secure and release folded flap portions 16a-d. Strip 18 may be any length sufficient to secure the extended flap portions 16a-d when folded to overlap target 14; however, the length of strip 18 is preferred to be the same length as the outer dimensions of sheet of permeable sheet 12. For example, the length of strip 18 may be the same length as an edge of sheet 12.

Malleable securing strip 18 can be any material that is formable or malleable, but it is preferred that strip 18 is either a metal wire or a strip of heavy metal foil. The wire or foil needs to have appropriate dimensions to allow for a one time use-easy closure and clamping, as well as, positive release of extended flap portions 16a-d (described in more detail below).

To use histological retaining device 10, a tissue sample is first harvested per known biopsy techniques. Second, the technician or other person who obtained the tissue sample will place the sample with its desired microtomy cutting plane face down on permeable target 14. It is important to orient the surface to be "outward" in relation to the wax embedding cast block, because this outward surface will be the surface first exposed to the plane of the microtome blade in section cutting. Placement of the tissue sample face down on target 14 does orient the cutting surface to be "outward." Third, if the sample is small or in pieces, a positioning gel or binder may be applied to fix the position of the tissue sample and in effect "pot" the tissue sample in place on permeable target 14. The positioning gel or binder is a glue or potting material that will accompany the specimens through the process and have similar cutting characteristics to the specimen. The envelope of potting materials available include low temperature melt (90° C. or less) agar agar and suitable molecular weight agarose diluted with $H_2O$ in variable concentration from 2-6% depending on the gel density desired. The potting agar or agarose will remain in a non-gel liquid state through desirable ranges of 50-60° C.

Referring to FIGS. 2a-e, there is illustrated an exemplary method on how histological retaining device 10 secures a tissue sample for histological processing. Once the tissue sample has been harvested and placed on target 14, as described above with or without the positioning gel or binder, the extended flap portions 16a-d are folded over target 14 one at a time to create packette 26 for retaining the tissue samples during processing. Packette 26 is created in four steps generally illustrated in FIGS. 2a-e.

Figure 2A:
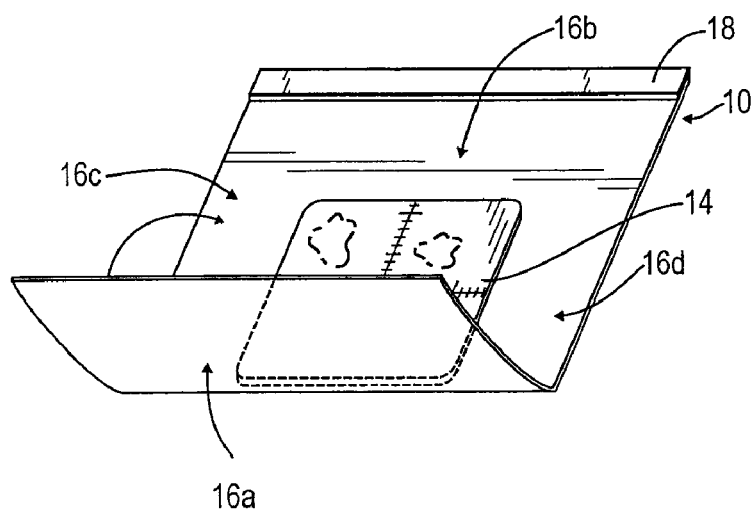
FIGS. 2a-e are an exemplary method of using the histological retaining device embodying the features of the present invention.
Figure 2B:
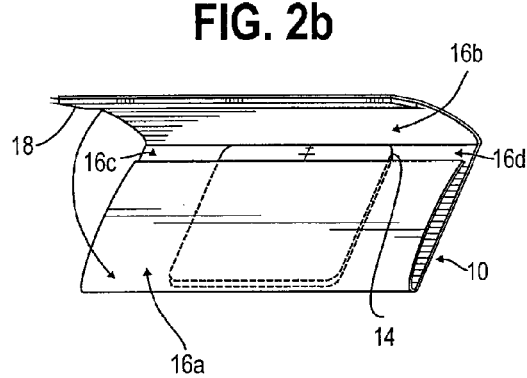
Figure 2C:
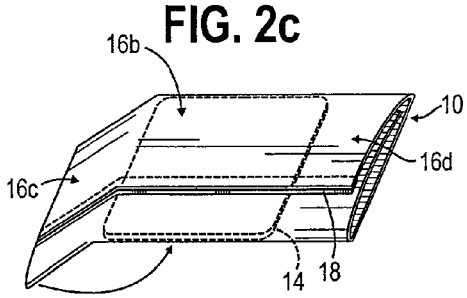
Figure 2D:
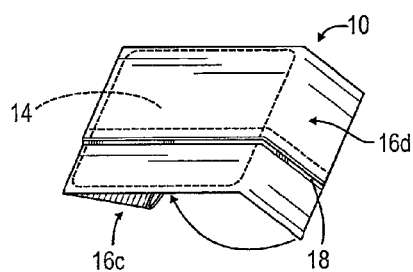
Figure 2E:
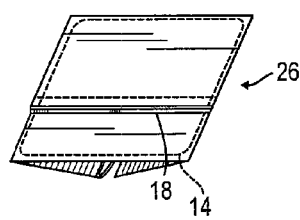

First, flap portion 16a is folded over target 14 as shown in FIG. 2a to overlap target 14. Second, flap portion 16b is also folded to overlap target 14 and flap portion 16a as shown in FIG. 2b. Third, flap portion 16c is folded under target 14 as shown in FIG. 2c to also overlap target 14. Lastly, flap portion 16d is then also folded under target 14 and under flap portion 16c to complete the packette 26 as shown in FIG. 2e by overlapping target 14 and flap portion 16c. At this point, securing strip 18 can be further crimped if desired to ensure that flap portions 16 are tightly secured to target 14; however, the folding of flap portions 16c and 16d should provide sufficient clamping force with securing strip 18 to secure the flap portions.

After packette 26 is formed, it is processed per known histological preparation and embedding methods. For example, packette 26 may be processed in a cassette such as is described in U.S. Pat. Nos. 5,080,869 or 5,928,934; incorporated herein by reference; or packette 26 could be processed in a embedding mold such as is described in U.S. Pat. No. 5,665,398; again, incorporated herein by reference. However, packette 26 could be processed by any typical method to prepare a tissue sample for histological examination.

Figure 3:
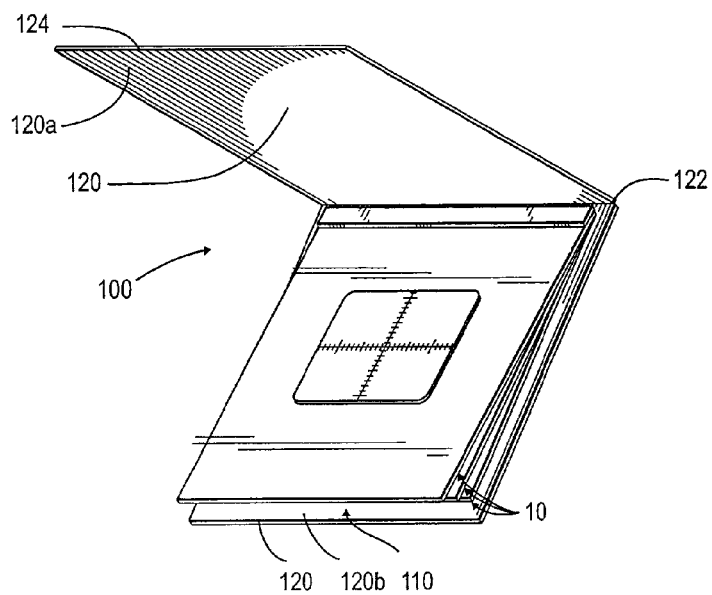
FIG. 3 is a perspective view of an exemplary assembly of histological retaining devices embodying further features of the present invention.

Referring to FIG. 3, there is illustrated an exemplary apparatus for packaging a plurality of histological specimen retaining devices. Assembly 100 generally consists of a stack 110 interposed between first and second cover portions 120a and 120b of protective cover 120.

Stack 110 is a plurality of histological retaining devices 10 in which an overlying device 10 is superimposed on an underlying device 10. FIG. 3 shows an example stack 110 of three superimposed histological retaining devices 10, but more or less devices may be included in stack 110. Protective cover 120 is hinged or folded at a midpoint to create fold 122. Fold 122, in turn, creates first and second cover portions 120a and 120b. Stack 110 is interposed between first and second cover portions 120a and 120b.

First and second cover portions 120a and 120b have a height and width sufficient to extend beyond a histological retaining device 10 that is interposed between first and second cover portions 120a and 120b. Consequently, when cover portions 120a and 120b are closed together, cover 120 completely covers stack 110. Generally, stack 110 rests on second cover portion 120b; however, each histological retaining device 10 of stack 110 may be detachably fixed to protective cover 120.

Protective cover 120 can be opened by lifting up first cover portion 120a at fold 122 with edge 124 to expose the top histological retaining device 10 to allow such device to be selected for use. First cover portion 120a can be closed by pressing down on first cover portion 120a to protect unused devices 10.

Another exemplary apparatus for packaging a plurality of histological specimen retaining devices is similar to a common box of tissue paper. Stack 110 may also consist of a plurality of interleaved histological specimen retaining devices 10. The interleaved stack of devices 10 may be contained in a protective box with at least one device 10 projecting out an opening disposed on the top surface of the box. An individual device 10 can be selected for use by pulling the projecting device 10 out of the box. The interleaving of the devices 10 causes the next device 10 to project out of the protective box.

It will be understood that various changes in the details, materials, and arrangements of parts and components which have been herein described and illustrated in order to explain the nature of the invention may be made by those skilled in the art within the principle and scope of the invention as expressed in the appended claims.

What is claimed is:

1. A method for processing tissue samples in preparation for histological examination, said method comprising:
   (A) providing a histological retaining device comprising
      (i) a foldable liquid permeable sheet having edges with a liquid permeable target disposed within the edges of said liquid permeable sheet, thereby providing extended flap portions which flap portions are foldable to overlap the liquid permeable target, and
      (ii) a malleable securing strip attached to the foldable liquid permeable sheet of a length sufficient to secure said folded flap portions overlapping said liquid permeable target;
   (B) creating a tissue preparation system comprising
      (i) placing a tissue sample on the liquid permeable target of said histological retaining device,
      (ii) folding the flap portions to overlap the liquid permeable target containing the liquid permeable tissue sample;
      (iii) crimping the malleable securing strip by bending the malleable securing strip around the folded flap portions to clamp the folded flap portions to the liquid permeable target; and
   (C) processing the tissue preparation system for histological examination in known ways, including passing liquid through the foldable liquid permeable sheet.

2. The method of processing tissue samples in preparation for histological examination according to claim 1, further comprising adding a binder to the tissue sample on the liquid permeable target prior to the folding of the flap portions.

3. The method of processing tissue samples in preparation for histological examination according to claim 2, wherein the binder is at least one of agar or agarose.

* * * * *